(12) United States Patent
Korn

(10) Patent No.: US 7,535,935 B2
(45) Date of Patent: May 19, 2009

(54) SPECTROSCOPIC CATHETER SYSTEM WITH WIDELY TUNABLE SOURCE AND METHOD OF OPERATION

(75) Inventor: Jeffrey A. Korn, Lexington, MA (US)

(73) Assignee: InfraReDx, Inc., Burlington, MA (US)

( * ) Notice: Subject to any disclaimer, the term of this patent is extended or adjusted under 35 U.S.C. 154(b) by 1217 days.

(21) Appl. No.: 10/259,076

(22) Filed: Sep. 27, 2002

(65) Prior Publication Data
US 2004/0064022 A1 Apr. 1, 2004

(51) Int. Cl.
H01S 3/00 (2006.01)

(52) U.S. Cl. ............... 372/20; 372/29.022; 372/8; 372/109; 600/476; 600/477; 600/478; 606/2; 606/3; 606/7; 606/8; 606/15; 359/330; 359/326; 359/332

(58) Field of Classification Search ........... 600/407, 600/160, 129, 473, 476, 477, 478, 342, 324–326; 372/20–33, 43, 19, 92, 98, 99, 8, 109; 606/2, 606/3, 7, 8, 15; 359/326–332
See application file for complete search history.

(56) References Cited

U.S. PATENT DOCUMENTS

| | | | | |
|---|---|---|---|---|
| 4,862,886 | A | 9/1989 | Clarke et al. ............. 128/303.1 |
| 4,998,932 | A * | 3/1991 | Rosen et al. ................. 606/29 |
| 5,176,675 | A | 1/1993 | Watson et al. ................ 606/15 |
| 5,428,635 | A | 6/1995 | Zhiglinsky et al. ............ 372/92 |
| 5,441,053 | A | 8/1995 | Lodder et al. ............... 128/664 |
| 5,491,714 | A | 2/1996 | Kitamura | |
| 5,733,277 | A | 3/1998 | Pallarito ..................... 606/7 |
| 5,769,791 | A * | 6/1998 | Benaron et al. ............. 600/473 |
| 5,772,597 | A * | 6/1998 | Goldberger et al. ......... 600/473 |
| 5,807,261 | A | 9/1998 | Benaron et al. | |
| 6,081,539 | A | 6/2000 | Mattori et al. ............... 372/20 |
| 6,130,899 | A | 10/2000 | Epworth et al. | |
| 6,134,003 | A | 10/2000 | Tearney et al. ............. 356/345 |
| 6,192,062 | B1 | 2/2001 | Sanchez-Rubio et al. ..... 372/92 |
| 6,212,216 | B1 | 4/2001 | Pillai ........................ 372/96 |
| 6,327,292 | B1 | 12/2001 | Sanchez-Rubio et al. ..... 372/92 |

(Continued)

FOREIGN PATENT DOCUMENTS

WO  WO 00/19889  4/2000

(Continued)

OTHER PUBLICATIONS

Bochove, E. J., "Theory of Spectral Beam Combining of Fiber Lasers," *IEEE Journal of Quantum Electronics*, vol. 38, No. 5, pp. 432- (May 2002).

Primary Examiner—Brian Casler
Assistant Examiner—Baisakhi Roy
(74) Attorney, Agent, or Firm—Houston Eliseeva, LLP

(57) ABSTRACT

A laser system for a spectroscopic catheter system uses multiple semiconductor gain media having gain peaks at different wavelengths. The output from the gain media is preferably coupled into single-mode fiber using conventional opto-electronic packaging techniques. As a result, the laser oscillator source has a spectral output that is wider than the gain bandwidth of a single medium to enable it to access the entire spectrum of interest, which is presently in the near infrared. Moreover, the semiconductor gain media can be packaged in a stable and controlled environment for long-term performance.

46 Claims, 8 Drawing Sheets

U.S. PATENT DOCUMENTS

| | | | |
|---|---|---|---|
| 6,343,227 B1 * | 1/2002 | Crowley | 600/407 |
| 6,345,059 B1 * | 2/2002 | Flanders | 372/20 |
| 6,421,164 B2 | 7/2002 | Tearney et al. | 359/287 |
| 6,459,919 B1 * | 10/2002 | Lys et al. | 600/407 |
| 6,485,413 B1 * | 11/2002 | Boppart et al. | 600/160 |
| 6,690,958 B1 * | 2/2004 | Walker et al. | 600/323 |
| 6,856,827 B2 * | 2/2005 | Seeley et al. | 600/426 |
| 6,980,573 B2 * | 12/2005 | Korn | 372/20 |
| 2001/0047137 A1 * | 11/2001 | Moreno et al. | 600/475 |
| 2002/0131049 A1 | 9/2002 | Schmitt | 356/479 |
| 2002/0168317 A1 * | 11/2002 | Daighighian et al. | 424/1.11 |

FOREIGN PATENT DOCUMENTS

| WO | WO 01/05004 | 1/2001 |
|---|---|---|
| WO | WO 01/08552 A1 | 2/2001 |

* cited by examiner

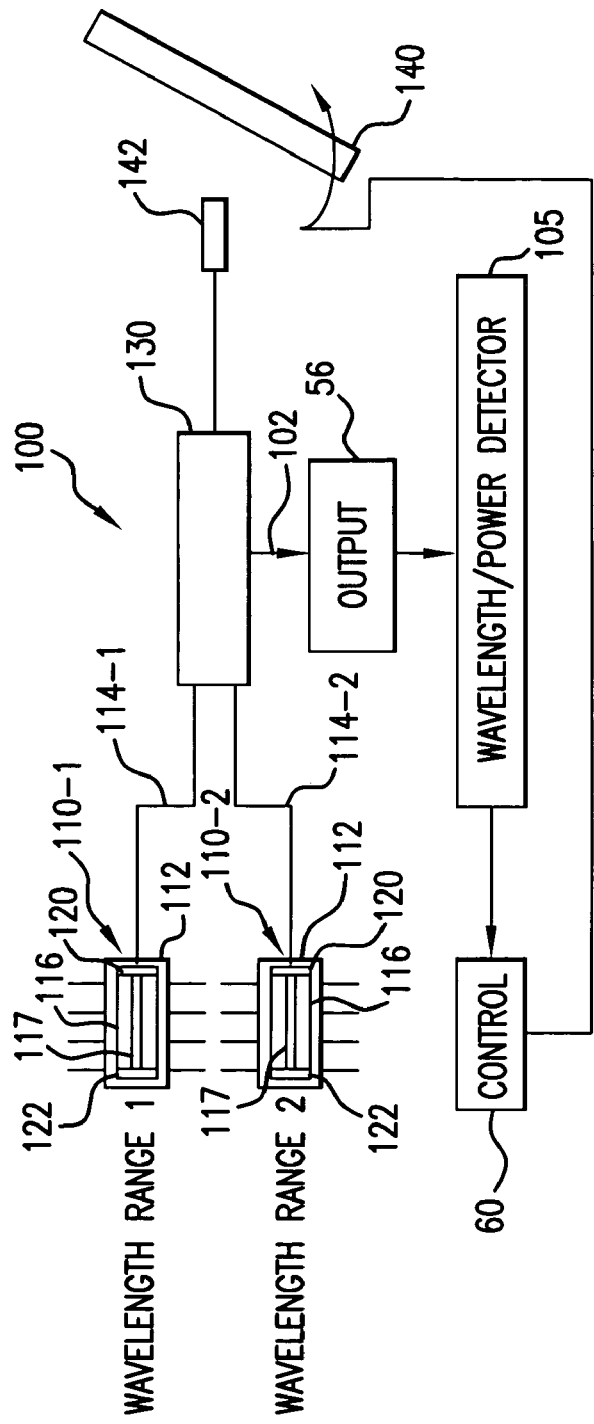
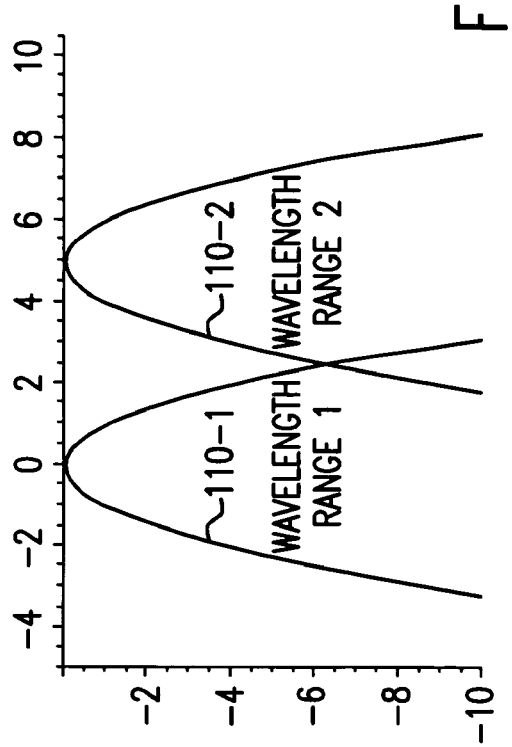
FIG.2
FIG.3

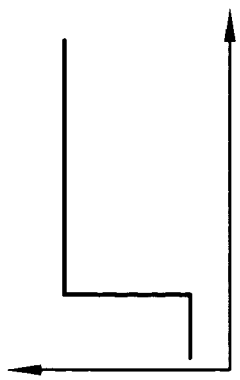
FIG. 4A
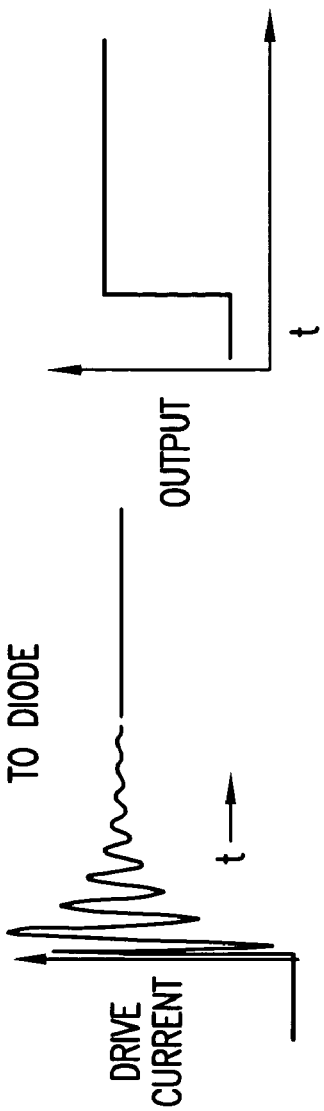
FIG. 4B
FIG. 4C
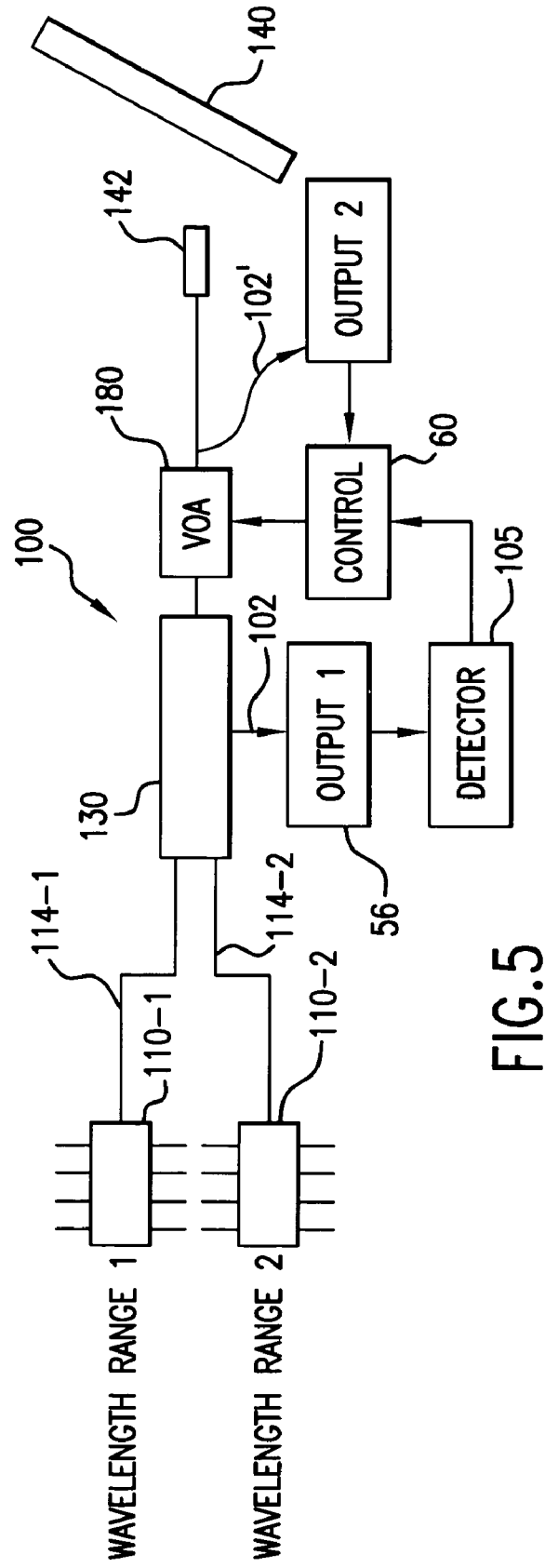
FIG. 5

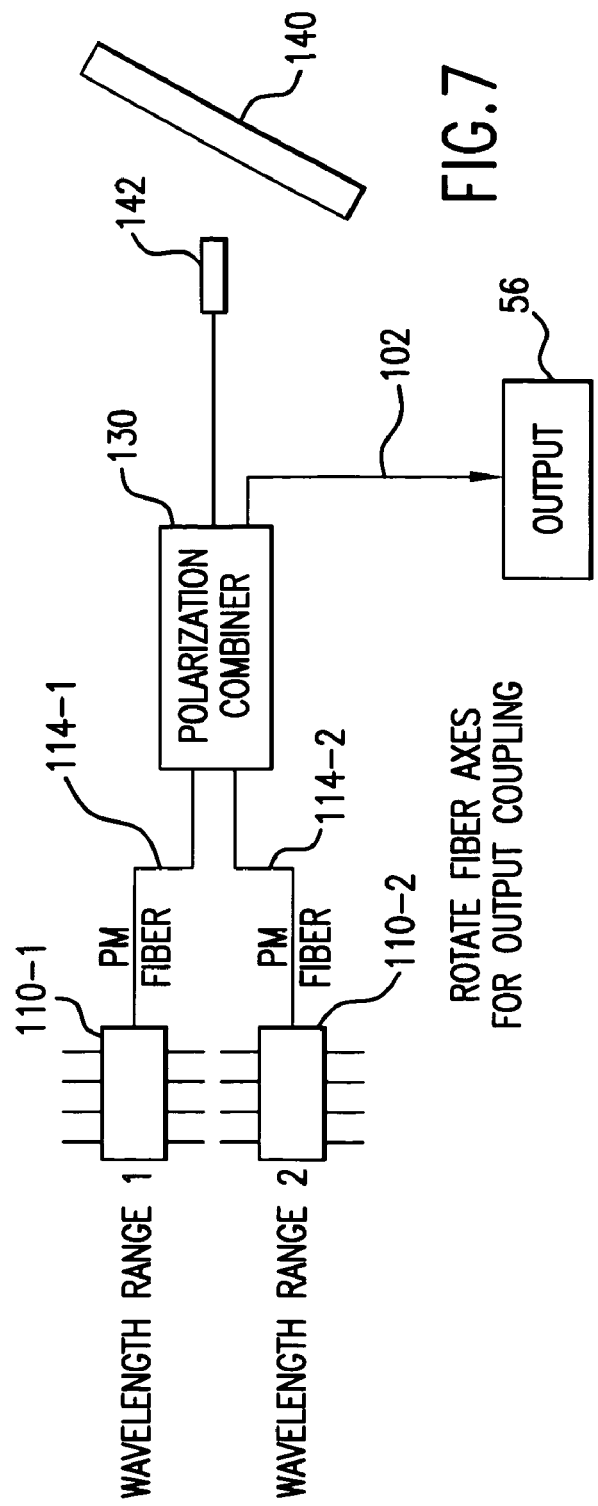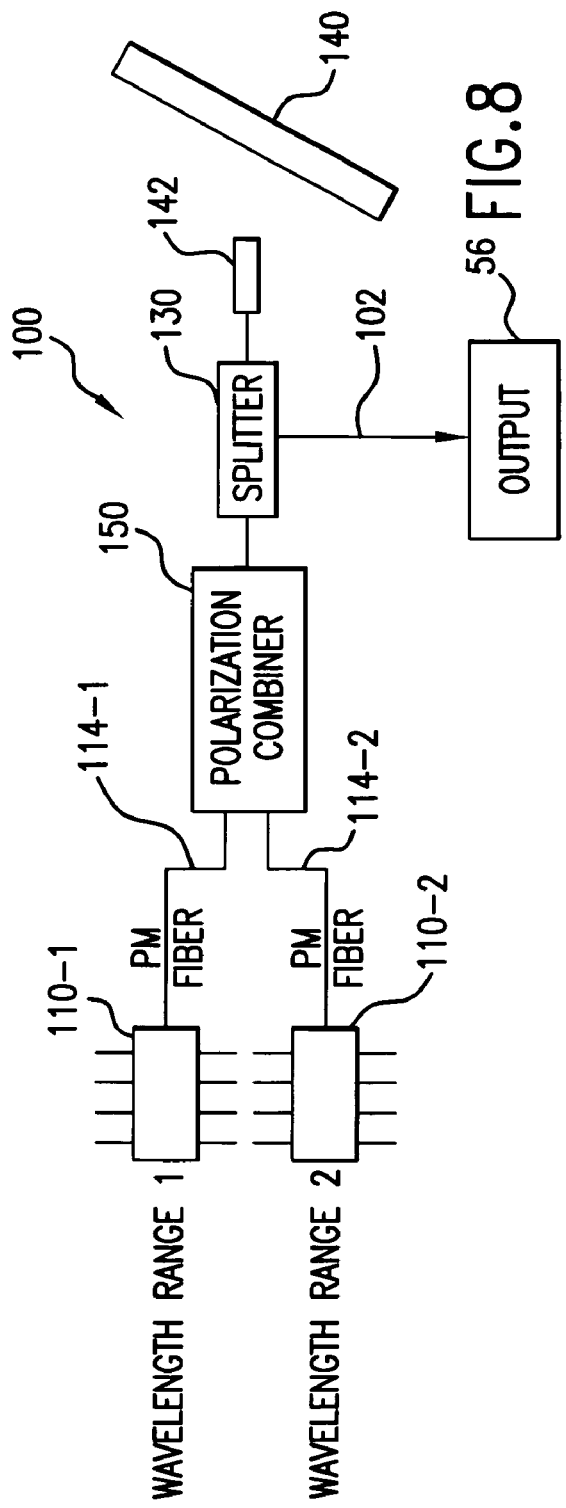

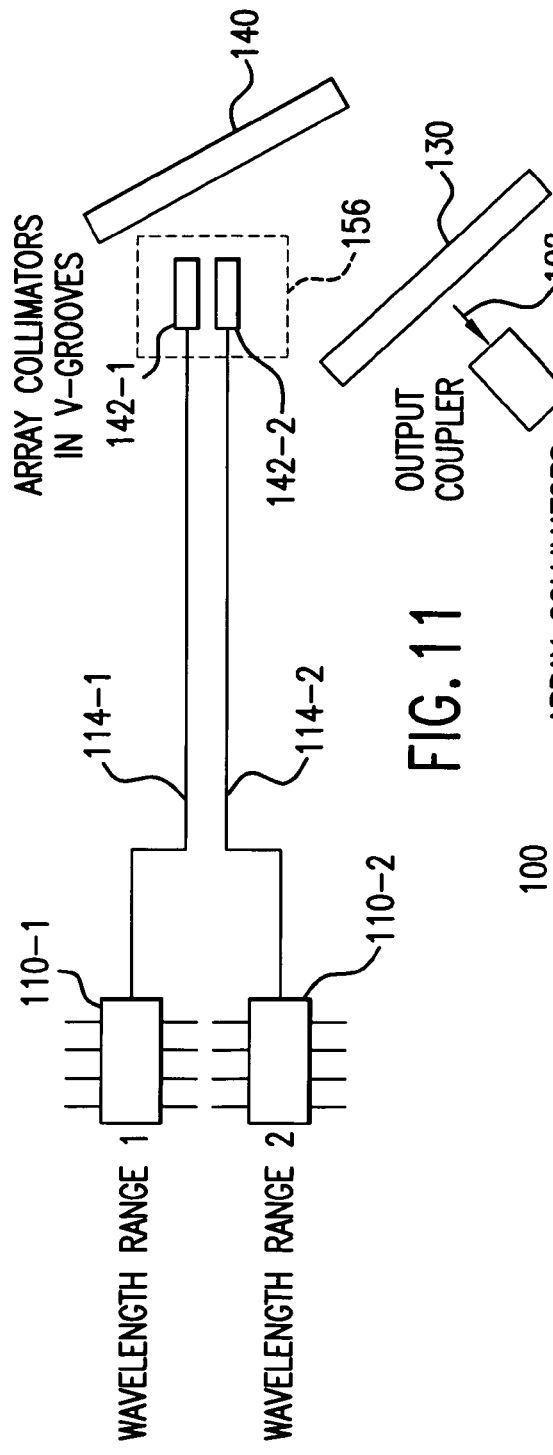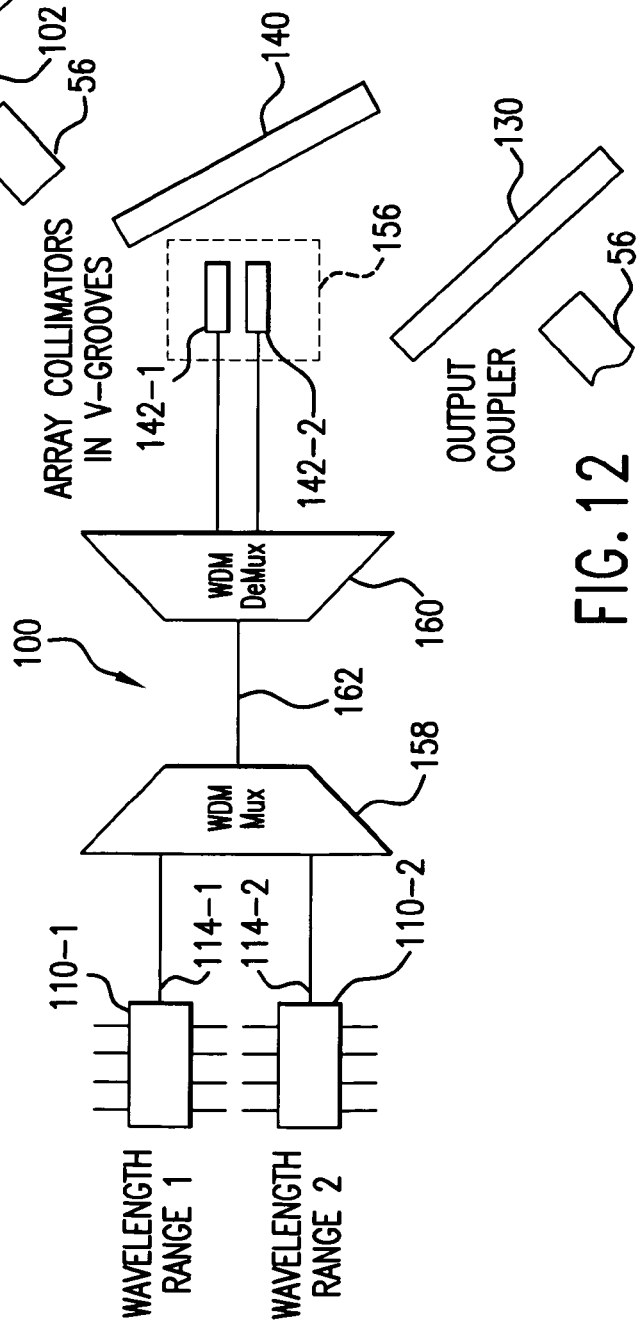

SPECTROSCOPIC CATHETER SYSTEM WITH WIDELY TUNABLE SOURCE AND METHOD OF OPERATION

BACKGROUND OF THE INVENTION

Tunable laser sources are applicable to a number of diagnostic and therapeutic medical applications. Optical coherence tomography is used to provide spatial resolution, enabling the imaging of internal structures. Spectroscopy is used to characterize the composition of structures, enabling the diagnosis of medical conditions, by differentiating between cancerous, dysplastic, and normal cellular structures. Fluorescence and exogenous chromospores can be used to increase the signal to noise ratio in these processes, providing for more accurate diagnostics.

One specific example of an application for spectroscopy concerns atherosclerosis. This is an arterial disorder involving the intimae of medium- or large-sized arteries, including the aortic, carotid, coronary, and cerebral arteries. Atherosclerotic lesions or plaques contain a complex tissue matrix, including collagen, elastin, proteoglycans, and extracellular and intracellular lipids with foamy macrophages and smooth muscle cells. In addition, inflammatory cellular components (e.g., T lymphocytes, macrophages, and some basophiles) can also be found in these plaques.

Disruption or rupture of atherosclerotic plaques appears to be the major cause of heart attacks and strokes, because after the plaques rupture, local obstructive thromboses form within the blood vessels. Although the risk of plaque rupture usually cannot be predicted, many postmortem examinations have revealed that this risk depends mainly on plaque composition. Most ruptured atherosclerotic plaques are characterized structurally by the formation of a large, soft, lipid-rich, necrotic core covered by a thin fibrous cap, densely infiltrated by macrophages. Of these features, lipid accumulation in so-called "lipid pools" is the most frequently observed precondition for rupture. Inflammation is also a major feature of nonruptured, but eroded, thrombosed plaques.

Near infrared (NIR) spectroscopy and statistical techniques can be used to extract useful information from the lower resolution NIR spectral data. For example, chemometrics, which combines spectroscopy and mathematics, can provide clear qualitative as well as quantitative information.

Specifically, efforts are being made to spectroscopically analyze blood vessel walls in vivo using infrared wavelengths to illuminate the blood vessel walls. The diffusely reflected light resulting from illumination of the walls can be analyzed either with blood in the vessel, or optionally with blood removed or replaced, e.g., temporarily, from the vessel.

SUMMARY OF THE INVENTION

The accuracy of the diagnosis of medical conditions using spectroscopy increases with increases in the wavelength band over which spectroscopic data are acquired. Many applications require scanning bandwidths of almost 100 nanometers (nm) and greater. Ideally, the spectral band would cover a large range of the infrared, between 850 nm and 1-2 micrometers ($\mu$m). Smaller ranges include 1100 to 1450 nm generally, or 1100 nm to 1350 nm, 1150 nm to 1250 nm, 1175 nm to 1280 nm, and 1190 nm to 1250 nm, more specifically.

Few existing technologies, however, can provide an optical signal that is tunable across such a large wavelength range and yet be compact, stable, and cost-effective. Semiconductor sources are relatively inexpensive, efficient, and small, but the gain bandwidths of optical amplifiers, for example, are limited to 0.1 to 100 nm, depending upon the particular material system used to fabricate the chips.

The present invention is directed to a laser system for a spectroscopic catheter system. The laser system uses multiple semiconductor gain media having gain peaks at different wavelengths. As a result, the laser oscillator source has a spectral output that is wider than the gain bandwidth of a single medium to enable it to access the entire spectrum of interest. The output from the gain media is preferably coupled into single-mode fiber using conventional, hermetic optoelectronic packaging techniques to provide a stable and controlled environment for long-term operation without performance degradation.

The architectures of the various embodiments can be divided into two classes: serial and parallel.

In the serial architectures, two or more gain media, with offset center wavelengths, are present in the laser cavity. A frequency selective element, such as a grating, is tuned first across a first wavelength range of the first gain medium, then tuned across a second wavelength range of the second gain medium, and so forth as depending on the number of addition gain media that are present. Thus, it tunes in a serial fashion.

Several schemes exist for combining the output from multiple gain media intra-cavity. One approach uses a power combiner or beam splitter, another takes advantage of the different states of polarization from two different gain media, still another uses a frequency selective or wavelength division multiplexing (WDM) filter to combine the output of the gain media, and lastly a switch may be used to switch between the various gain media.

In the parallel architectures, multiple gain media are combined, and as the frequency selective element is tuned such that both gain media receive feedback simultaneously and in parallel. Thus, multiple spectral lasing peaks will appear at the output, and as the frequency selective element is tuned these peaks will be scanned simultaneously allowing access to multiple wavelength regions. Approaches for combining the gain media include using a frequency selective mirror (WDM), and offsetting the angle of incidence of the light sources on a diffraction grating.

In general, according to one aspect, the invention features a widely tunable source spectroscopic catheter system. This system comprises a catheter for insertion into a patient to transmit light to the patient. A tunable laser source is provided that includes at least two semiconductor optical amplifier (SOA) chips and at least one frequency selected tunable element for controlling a frequency of light fed back into the at least two SOA chips. An output coupler couples light from the at least two SOA chips into the catheter. Finally, at least one detector is provided for detecting light returning from the patient to thereby enable the spectroscopic analysis.

In the anticipated application, the catheter is inserted into a lumen of the patient, such as a blood vessel. It is currently used for the diagnosis of atherosclerosis.

In the current implementation, the at least two semiconductor optical amplifier chips are reflective SOA chips. They are preferably packaged in separate, pigtailed opto-electronic modules, which help to ensure their long-term stable operation. They can be fabricated using a InGaAs or AlInGaAs material system.

The at least two SOA chips have different gain bandwidths. As a result, they can work cooperatively to increase the spectral bandwidth of the system over the bandwidth of a single element or chip.

Different implementations can be used for the output coupler. In one embodiment, an N-by-N coupler is used for coupling light between the at least one frequency selective tunable element and the at least two SOA chips and the catheter.

In another embodiment, the output coupler is a splitter. Further, polarization combiners can be used to combine the light from the at least two SOA chips. A switch can also be used to switch between the SOA chips.

In still other embodiments, the output coupler can be implemented as a partially reflective mirror that provides both feedback and the laser output port.

In still other embodiments, combinations of multiplexers/demultiplexors can be used to combine light from the SOA chips.

To control power levels, variable optical attenuators are preferably used.

Tuning is currently achieved by controlling the angle of a diffractive grating to thereby control the spectral feedback into the SOA chips. In some embodiments, the system operates to feed back light into the SOA chips serially in time. In other embodiments, it is fed back simultaneously to thereby enable the accessing of two different parts of the spectrum simultaneously.

In general, according to another aspect, the invention also features a method for providing tunable frequency light to a patient. This method comprises inserting a catheter into the patient. Then, light is generated in at least two SOA chips. The frequency of the light fed back into the SOA chips is controlled to tune the wavelength of operation. Finally, light from the at least two SOA chips is coupled into the catheter.

Further, in still another embodiment, the invention features a widely tunable source. This source comprises a first pigtailed semiconductor gain module with a first gain bandwidth and a second pigtailed semiconductor gain module with a second gain bandwidth. A frequency selective tunable element is coupled to the first pigtail of the first pigtailed semiconductor gain module and the second pigtail of the second pigtailed semiconductor gain module. The frequency selective tunable element controls a frequency of light fed back into the semiconductor gain modules. An output coupler is provided for coupling light from the semiconductor gain modules into an output waveguiding device, such optical fiber. A controller controls the frequency selective tunable element to change a wavelength of generated light.

The present invention provides a number of advantages over other solutions. First, it can be low cost and mass-produced since it leverages technologies available for the telecommunications industry. Moreover, these hermetic modules can be small and exhibit highly stable operation over wide ambient temperature ranges and time.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings:

FIG. 2 is a schematic block diagram of a tunable laser source, according to the present invention;

FIG. 3 is a plot of gain (arbitrary units) as a function of bandwidth (arbitrary units) for the two SOA chips;

FIGS. 4A, 4B, and 4C are plots of the relaxation oscillation of a laser cavity as a function of time, applied current to the semiconductor chip as a function of time, and the output after relaxation oscillation suppression as a function of time;

FIG. 5 is a schematic block diagram of a widely tunable source according to another configuration;

FIG. 7 is a schematic block diagram of a widely tunable source according to a second embodiment of the present invention;

FIG. 8 is a schematic block diagram of a third embodiment of the widely tunable source of the present invention;

FIG. 11 is a schematic block diagram of a sixth embodiment of the widely tunable source according to the present invention;

FIG. 12 is a schematic block diagram of a seventh embodiment of the widely tunable source according to the present invention.

DETAILED DESCRIPTION OF THE PREFERRED EMBODIMENTS

Figure 1:
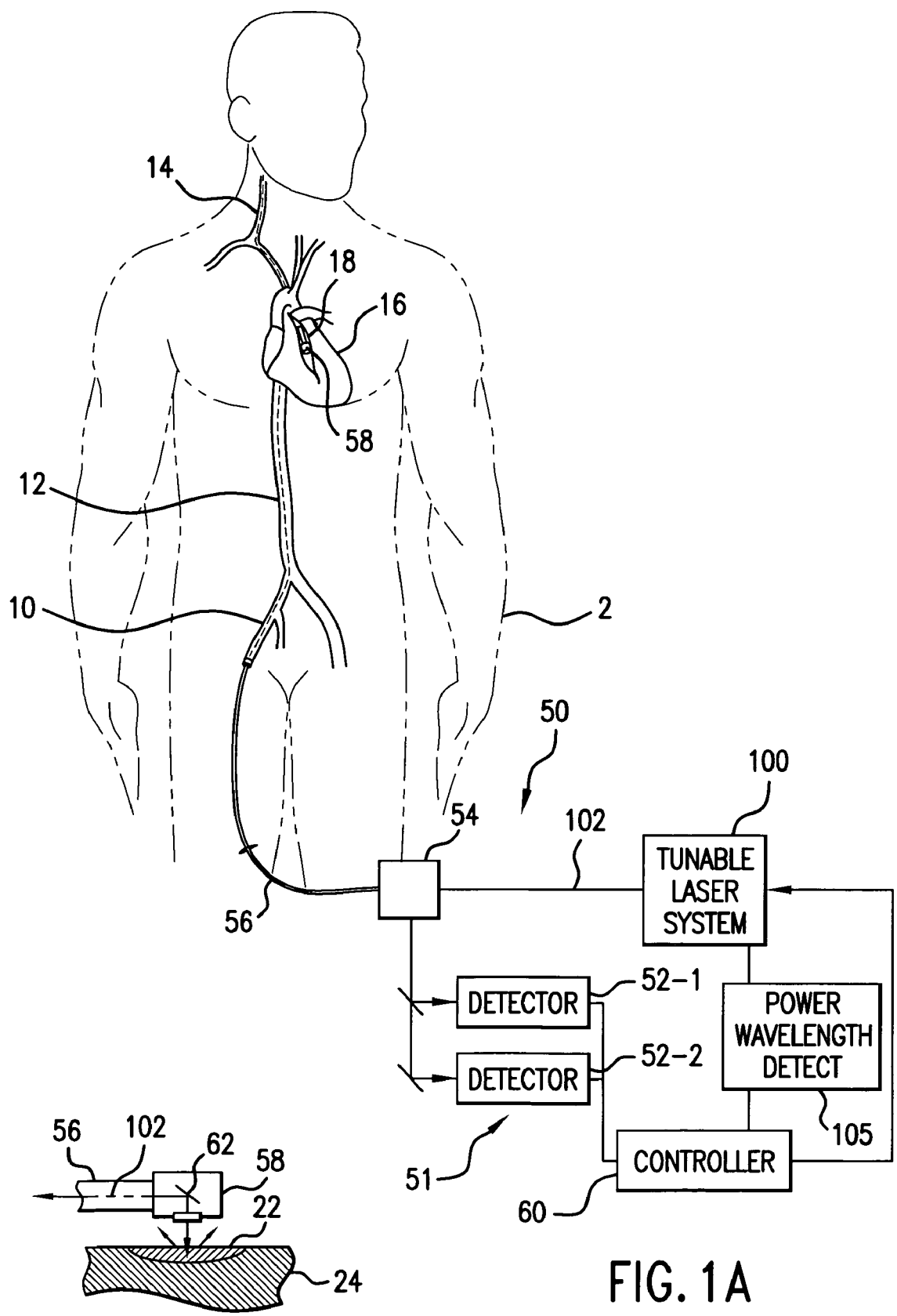
FIG. 1A is a schematic block diagram illustrating the spectroscopic catheter system with the tunable laser system of the present invention.
FIG. 1B is a cross-sectional view of the catheter head performing spectroscopic analysis on a target region of a blood vessel.

FIG. 1A shows a spectroscopic catheter system 50 to which the tunable laser system 100, of the present invention, is applicable.

Specifically, the catheter system 50 comprises a catheter 56 that includes an optical fiber or optical fiber bundle. The catheter 56 is typically inserted into the patient 2 via a peripheral vessel, such as the femoral artery 10. The catheter head 58 is then moved to a desired target area, such as a coronary artery 18 or the carotid artery 14. In the example, this is achieved by moving the catheter head 58 up through the aorta 12.

When at the desired site, tunable near infrared radiation (NIR) is generated by a tunable laser system 100 across the spectral band of interest. It is coupled into the optical fiber of the catheter 56 to be transmitted to the catheter head 58.

In more detail, with reference to FIG. 1B, the tunable optical signal 102 for the optical fiber of the catheter 56 is directed by a fold mirror 62, for example, to exit from the catheter head 58 and impinge on the target area 22 of the artery wall 24. The catheter head 58 then collects reflected and scattered radiation from the target area 22 to transmit it back down the optical fiber of the catheter 56 to a splitter or circulator 54. This provides the returning radiation to a detector system 51. In the illustrated example, the detector system 51 comprises multiple, such as two, detectors 52-1 and 52-2.

The controller 60 monitors the response of the detector system 51, while controlling the tunable laser system 100 in order to probe the near infrared spectral response of the target area 22. The tunable laser system 100 is by monitored the controller 60 with a power and wavelength detector subsystem 105. This enables the controller 60 to track both the wavelength and power output of the tunable laser system 100.

FIG. 2 shows the general configuration of a tunable laser system 100, which has been constructed according to the principles of the present invention.

Specifically, it comprises two semiconductor opto-electronic modules 110-1 and 110-2 in the illustrated embodiment. In other embodiments, where wider tuning ranges are required, more modules can be used, such as four to eight, or more depending on the spectral range of interest.

Each of the modules 110-1, 110-2 comprises a semiconductor chip 116. In the preferred implementation, the chip 116 is a semiconductor optical amplifier chip, and specifically a reflective SOA. The chips' back facets 122 have a highly reflective (HR) coating. The front facets have an anti-reflective (AR) coating 120. As a result, the chips' gain waveguides 117 act as broadband optical energy sources.

Light exiting from the front facets 120 of the chips 117 is coupled into respective pigtails 114-1 and 114-2. Preferably, these pigtails 114-1, 114-2 are single mode fiber that extend through fiber feed-throughs in the hermetic packages 112 of the modules 110-1 and 110-2. These hermetic packages 112 can be dual inline (DIP) or butterfly packages depending on the implementation.

In still other embodiments, standard, double pigtailed SOA modules can be used. In this case, back reflector feedback is preferably provided with fiber Bragg gratings formed in one of the pigtails or by flat cleaving the pigtails and then HR coating the fiber facets.

Each of the pigtails 114-1 and 114-2 from the semiconductor modules 110-1 and 110-2 is received by an output coupler 130. This output coupler 130 provides an output port for the laser cavity, which includes the SOA chips 116 of the modules 110-1 and 110-2. This output coupler 130 provides the output optical signal 102 that is coupled into the catheter 56. Some of the output, however, is used by the power and wavelength detector 105 to provide for feedback control of the tunable laser system 100 by the controller 60.

Optical energy that is not provided as the output signal 102 is coupled to a frequency selective tunable element 140 via free space transmission using a collimator 142. In one example, the collimator 142 is a graded index or other type of lens.

The frequency selective tunable element 140 provides tunable, narrow band feedback into the SOA chips 116 of the semiconductor modules 110-1 and 110-2. In the present implementation, the frequency selected tunable element 140 is a diffraction grating. It is angle tuned under the control of the controller 60 to thereby modulate or change the narrow band feedback to the modules 110-1 and 110-2 and thus control the wavelength of the output signal 102.

In a current implementation, the angle of the grating 140 is controlled using a resonant Galvanometer. It preferably is tuned to scan the spectrum in less than 50 milliseconds to remove motion artifacts do to the beating of the heart. Presently, the spectrum is scanned in less than 10 ms or preferably 5 ms or less.

In some of the other embodiments discussed hereinbelow, other types of frequency selective tunable elements can be used. For example, in the serial configurations, acousto-optic filters and Bragg gratings can be used in place of the diffraction grating.

The presently proposed configuration incorporates a 600 line/millimeter (mm) diffraction grating, which is 12×12×6 mm in size (Optometrics, LLC, Part No. 3-4669).

FIG. 3 shows the gain bandwidths of the chips 116 for the modules 110-1 and 110-2. Specifically, they are spectrally distributed, covering different gain bandwidths. As a result, the tunable laser system has a wider bandwidth of operation than the bandwidths of each of the modules 110-1 and 110-2 individually. In this way, the system is widely tunable to enable spectroscopic analysis over a wide bandwidth, such as the near infrared spectrum.

FIGS. 4A-4C illustrate the control executed by the controller 60 through the monitoring of the power and wavelength detector 105 in order to get a stable power output from the tunable laser system 100.

Specifically, as illustrated in FIG. 4A, the SOA chips 117 of modules 110-1 and 110-2 can be susceptible to relaxation oscillations in the laser cavities of their respective gain waveguides 117. Specifically, the output signal 102 can ring in response to tuning into the gain spectrum, which causes the gain media to convert from a high gain, low output state to a saturated state. Concerns exist that the peak powers occurring during this oscillation could induce damage.

FIG. 4B illustrates an exemplary drive current to the chips 116 of the modules 110-1, 110-2. Specifically, if the drive current is selected to be counter-cyclical to the natural relaxation oscillations of the laser cavities, then the output will produce a step output, as illustrated in FIG. 4C.

FIG. 5 illustrates another general configuration of the inventive tunable laser system 100. As discussed previously, two or more modules 110-1, 110-2 are used as gain for the laser cavity. They couple optical energy into pigtails 114-1, 114-2, which is received by the output coupler 130. The output coupler 130 provides the output signal to the catheter 56.

The controller 60, however, monitors the output using the power/wavelength detector 105 and modulates the attenuation provided by a variable optical attenuator 180 in the laser cavity. This variable optical attenuator 180 regulates the level of attenuation in or the quality factor of the cavity. This enables the controller 60 to monitor the power level of the output signal 102 and then change the power by control of the attenuation level using VOA 180.

On other embodiments, the output is taken from the grating-side of the VOA 180, see reference numeral 102'.

Figure 6:
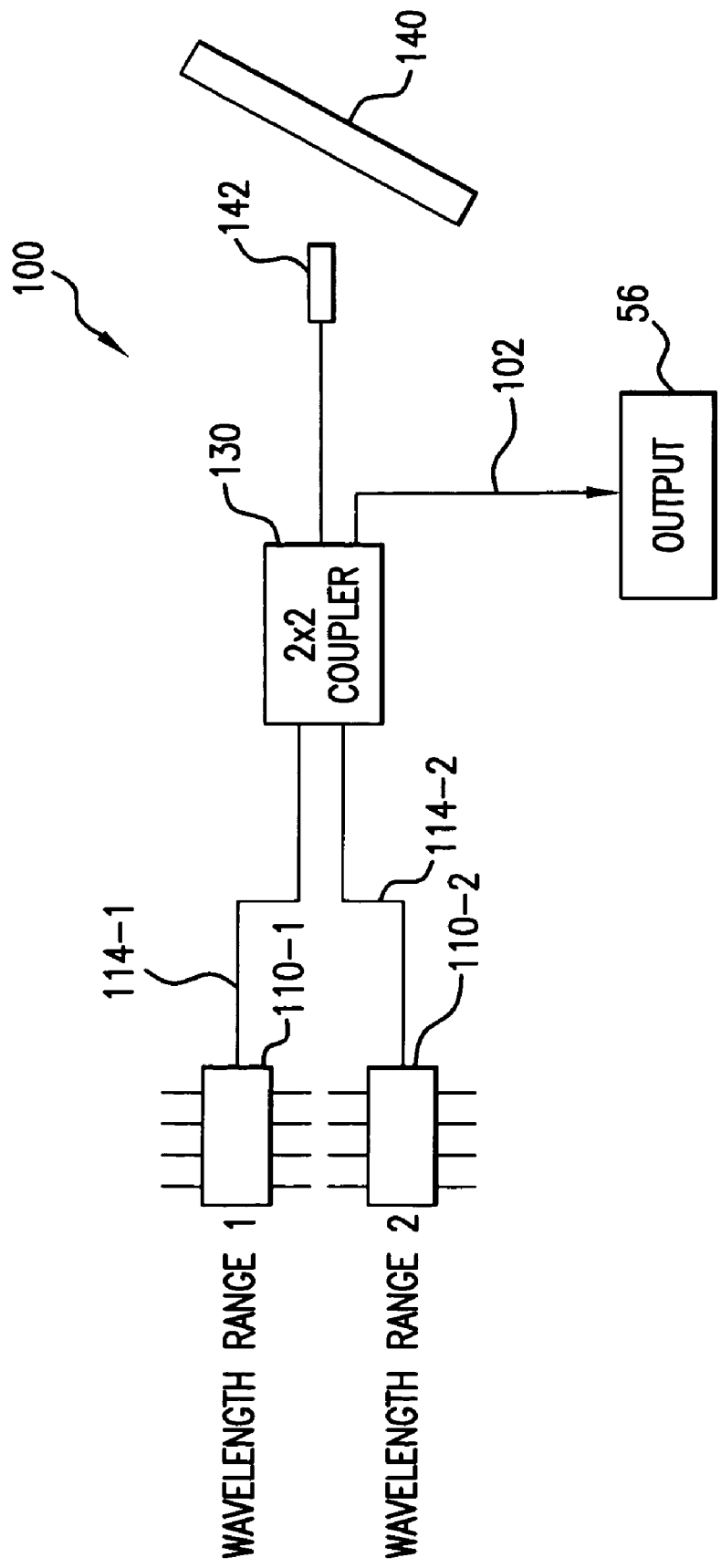
FIG. 6 is a schematic block diagram of a first embodiment of the widely tunable source according to the present invention.

FIG. 6 illustrates a first specific embodiment of the tunable laser system 100. Specifically, each of the pigtails 114-1, 114-2 from the laser modifies 110-1, 110-2 is connected to a two-by-two coupler that functions as the output coupler 130. In one implementation, the two-by-two coupler is a a fused biconical tapered fiber device. A third port of the two-by-two coupler is connected to the free space collimator 142, which provides signal to and from the frequency selective tunable element 140. The fourth port of the two-by-two coupler 130 provides the output signal 102 to the catheter 56.

During operation, the first embodiment is tuned by progressively controlling the tilt of the frequency selective tunable element 140. As its feedback passes through the gain bandwidth of the SOA chip of first module 110-1, the first module provides the optical gain in the laser cavity. Then, as the frequency selective tunable element rotates further, its feedback passes through the gain bandwidth of the second module 110-2, which then provides the gain to the cavity.

FIG. 7 shows a second specific embodiment of the tunable laser source 100, which uses polarization diversity to achieve a low loss combination of the outputs from the two modules. The fiber pigtails 114-1, 114-2 from the modules 110-1, 110-2 comprise polarization-maintaining (PM) fiber. This fiber maintains the polarization state of the typically highly polarized energy from the chips 117 of the modules 110-1, 110-2.

One of the pigtails 114-1, 114-2 has an axis that is rotated 90 degrees with respect to the other fiber at a polarization combiner/output coupler 130. As a result, the optical energy from the modules 110-1, 110-2 is combined and provided to the free space collimator 142 and then to the frequency selected tunable element 140, which provides the narrowband feedback. Additionally, optical energy is also provided as the output signal 102 to the catheter 56.

FIG. 8 shows a third embodiment of the tunable laser source 100. This embodiment, similar to the second embodiment, uses a polarization combiner. In this example, the polarization combiner 150 simply functions to combine the energy from the polarization maintaining fiber pigtails 114-1, 114-2. A splitter functions as the output coupler 130. Specifically, the splitter 130 functions an intra cavity tap to provide the output signal 102.

Figure 9:
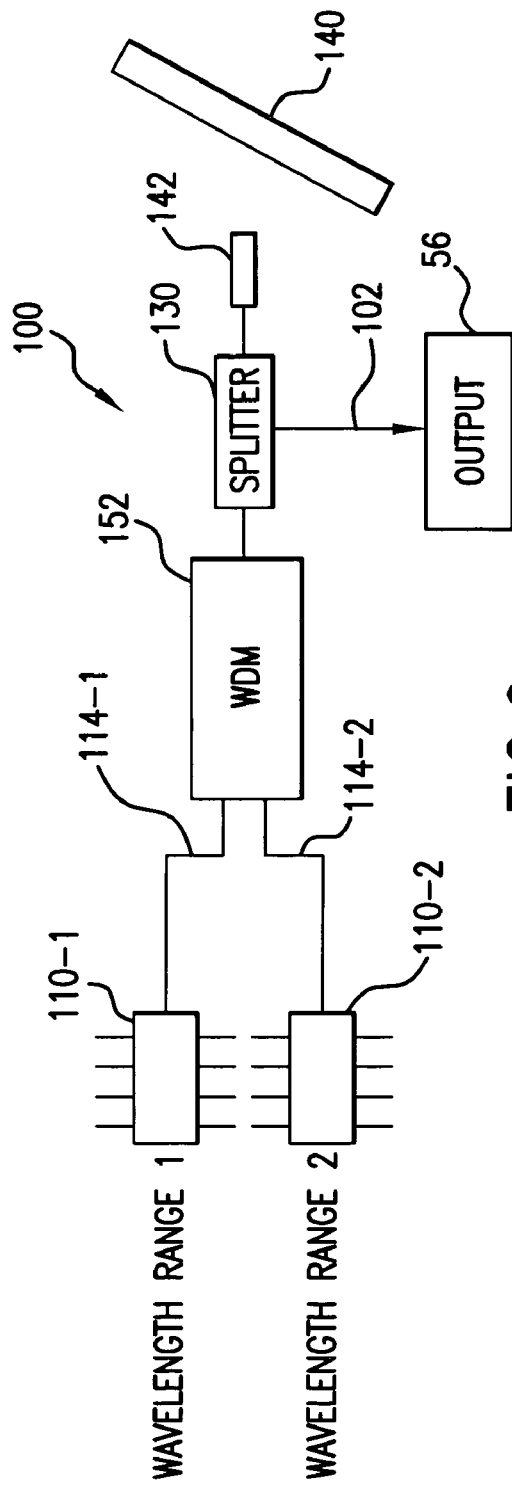
FIG. 9 is a schematic block diagram of a fourth embodiment of the widely tunable source of the present invention.

FIG. 9 shows a fourth embodiment of the optical laser source 100. In this example, a WDM combiner 152 is used to combine and split the optical signals on the pigtails 114-1, 114-2 from the modules 110-1, 110-2. WDM combiner 152 is typically a thin film dichroic filter. It uses the spectrally distributed outputs from the two modules 110-1, 110-2 to combine their respective optical signals. A splitter/output coupler 130 couples to the frequency selectable tunable element 140 via the free space collimator 142 and provides the tap for the output signal 102.

The fourth embodiment has spectral dead zone due to the transition in the WDM filter 152. This dead zone will typically consume about 0.5 nanometers of the tuning curve. Further, power can be doubled by polarization combining two modules for each wavelength band.

Figure 10:
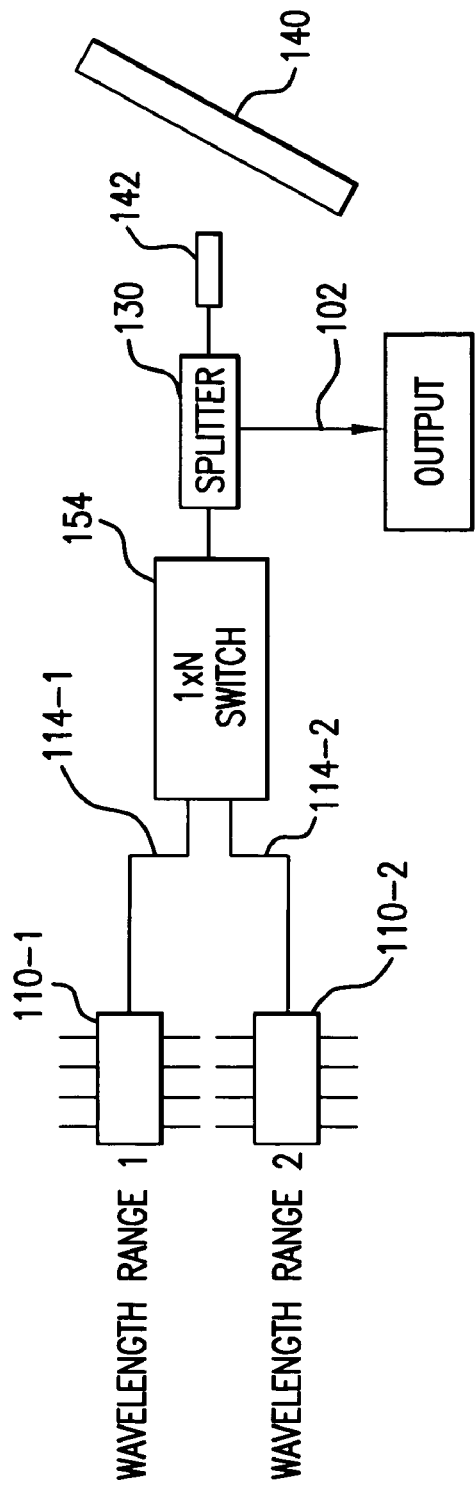
FIG. 10 is a schematic block diagram of a fifth embodiment of the widely tunable source according to the present invention.

FIG. 10 illustrates a fifth embodiment of the tunable laser system 100. In this example, a one-by-two switch 154 is used to select one of modules 110-1, 110-2, and provide its output to a splitter/output coupler 130. In this example, only one of the laser modules 110-1, 110-2, is providing the gain to the laser cavity at any moment during operation.

In other embodiments, where additional modules combined, this system can be scaled to wider bandwidths of operation by increasing the port count of the switch 154 to a one-by-n switch, where n equals the number of modules.

The fifth embodiment, however, provides a non-zero switching time of a few milliseconds due to the operation of the switch 154. This creates a limited spectral dead zone. On the other hand, power can be doubled by polarization combining the output from two modules at each switch port.

FIG. 11 shows a sixth embodiment of the present invention. Here, each of the pigtails 114-1, 114-2 from the respective modules 110-1, 110-2 terminates in respective free space collimators 142-1, 142-2. In one example, these collimators are held in a V-groove silicon bench 156, to provide a stable, free space interface with the frequency selective tunable element 140.

The angle tuning of the frequency selective tunable element 140 provides different spectral feedback into each of the modules 110-1, 110-2, with the output being taken through the partially reflecting mirror/output coupler 130. As a result, the output signal 102 into the catheter will include two distinct, spectrally separated signals associated with the simultaneous operation of the modules 110-1, 110-2. As a result, this system can be used to simultaneously scan two regions of the spectrum of interest.

In order to provide the different spectral feedback, the angle of incidence for light from the two collimators 142-1, 142-2 must be different. In one implementation, this is achieved with a silicon bench in which the collimators 142-1, 142-2 are held in a non-parallel relationship. In another implementation, an intervening lens is used to create angle of incidence diversity between the beams from the collimators 142-1, 142-2.

The sixth embodiment is scalable to n wavelength ranges, by adding modules 110 and corresponding collimators 142 in the V-groove array 156.

With reference to FIG. 1A, in this sixth embodiment, the number of detectors 52 matches the number of modules 110 used. Specifically, there is a detector 52-n for each module 110-n to thereby enable the simultaneous detection of the spectral components in the output signal 102.

FIG. 12 shows a seventh embodiment of the tunable laser system 100. This uses a combination of a WDM multiplexer 158 and WDM demultiplexor 160 in a Littrow configuration. As a result, the output from each of the modules 110-1, 110-2 is combined onto a single fiber 162 and then demultiplexed to be coupled through the respective free space collimators 142-1, 142-2 to the frequency selective tunable element 140. A partially reflecting mirror acts as the output coupler 130 and laser cavity mirror.

Although the seventh embodiment shows two modules 110-1, 110-2, it is scalable to n wavelength ranges. Moreover, power in each band can be doubled by polarization combining two modules before the WDM multiplexer 158.

Figure 13:
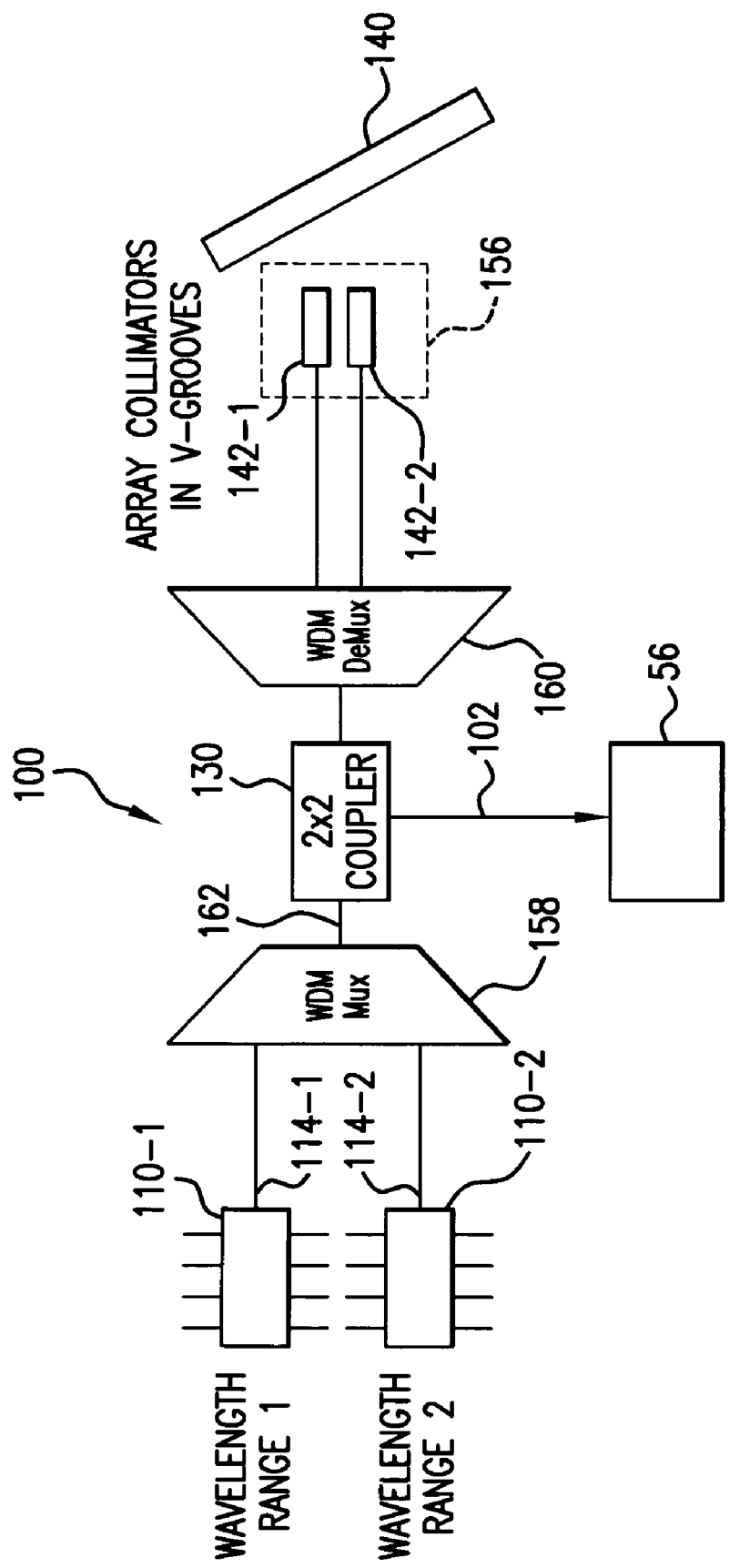
FIG. 13 is a schematic block diagram of an eighth embodiment of the widely tunable source according to the present invention.

FIG. 13 shows an eighth specific embodiment of the present invention. This is a variant of the seventh embodiment. Specifically, a two-by-two/output coupler functions as an intracavity splitter. It is placed on the fiber link 162 between the WDM multiplexer 158 and the demultiplexor 160. This provides the output signal 102 to the catheter 56.

While this invention has been particularly shown and described with references to preferred embodiments thereof, it will be understood by those skilled in the art that various changes in form and details may be made therein without departing from the scope of the invention encompassed by the appended claims.

What is claimed is:

1. A widely tunable source spectroscopic catheter system, comprising:
    a catheter for insertion into a patient to transmit light to the patient;
    a tunable laser source including:
        at least two semiconductor optical amplifier chips,
        at least one frequency selective tunable element for controlling a frequency of light fed back into the at least two semiconductor optical amplifier chips, and
        an output coupler for coupling light from the at least two semiconductor optical amplifier chips into the catheter; and
    at least one detector for detecting light returning from the patient to perform spectroscopic analysis.

2. A catheter system as claimed in claim 1, wherein the catheter is inserted into a lumen of the patient.

3. A catheter system as claimed in claim 1, wherein the catheter is inserted into a blood vessel of the patient.

4. A catheter system as claimed in claim 1, wherein the catheter is inserted into a blood vessel to a heart of the patient.

5. A catheter system as claimed in claim 1, further comprising at least one pigtailed optoelectronic package for housing the at least two semiconductor optical amplifier chips.

6. A catheter system as claimed in claim 1, wherein the at least two semiconductor optical amplifier chips have different gain bandwidths.

7. A catheter system as claimed in claim 1, wherein the output coupler comprises an nxn coupler for coupling light between the at least one frequency selective tunable element and the at least two semiconductor optical amplifier chips and the catheter.

8. A catheter system as claimed in claim 1, wherein the output coupler comprises a splitter for coupling light between the at least one frequency selective tunable element and the at least two semiconductor optical amplifier chips and the catheter.

9. A catheter system as claimed in claim 1, further comprising a polarization combiner for combining light from the at least two semiconductor optical amplifier chips and providing the light to the at least one frequency selective tunable element.

10. A catheter system as claimed in claim 1, further comprising a switch for selectively coupling the at least two semiconductor optical amplifier chips to the at least one frequency selective tunable element and the output coupler.

11. A catheter system as claimed in claim 1, wherein the output coupler comprises a partially reflective mirror for feeding back light into the at least two semiconductor optical amplifier chips and outputting light to the catheter.

12. A catheter system as claimed in claim 1, further comprising a multiplexer and demultiplexer for combining light from the at least two semiconductor optical amplifier chips and providing the light to the at least one frequency selective tunable element and for dividing light returning from the at least one frequency selective tunable element between the at least two semiconductor optical amplifier chips.

13. A catheter system as claimed in claim 1, further comprising a variable optical attenuator for controlling a level of the light provided to the catheter.

14. A catheter system as claimed in claim 1, wherein the at least one frequency selective tunable element comprises a diffractive grating.

15. A catheter system as claimed in claim 14, further comprising a grating angle controller for modulating an angle of the diffractive grating relative to light from the at least two semiconductor optical amplifier chips.

16. A catheter system as claimed in claim 1, further comprising a controller for tuning a frequency of light fed back into the at least two semiconductor optical amplifier chips from the at least one frequency selective tunable element.

17. A catheter system as claimed in claim 1, wherein the controller tunes the at least one frequency selective tunable element to feed back light into the at least two semiconductor optical amplifier chips serially in time.

18. A catheter system as claimed in claim 1, wherein the controller tunes the at least one frequency selective tunable element to feed back light into the at least two semiconductor optical amplifier chips simultaneously.

19. A catheter system as claimed in claim 1, further comprising:
a power monitor for monitoring a level of the light in the catheter; and
a controller for tuning a frequency of light fed back into the at least two semiconductor optical amplifier chips from the at least one frequency selective tunable element and for controlling the level of the light in the catheter in response to the power monitor.

20. A catheter system as claimed in claim 19, wherein the controller regulates the level of the light in the catheter by regulating a drive level of the at least two semiconductor optical amplifier chips.

21. A catheter system as claimed in claim 19, wherein the controller regulates the level of the light in the catheter by control of a variable optical attenuator.

22. A catheter system as claimed in claim 1, further comprising:
a frequency monitoring device for measuring spectral characteristics of the light in the catheter; and
a controller for tuning the at least one frequency selective tunable element in response to the frequency monitoring device.

23. A catheter system as claimed in claim 1, wherein a common frequency selective tunable element provides light feed back into the at least two semiconductor optical amplifier chips.

24. A method for providing tunable frequency light to a patient, the method comprising:
inserting a catheter into a patient;
generating light in at least two semiconductor optical amplifier chips;
controlling a frequency of light fed back into the at least two semiconductor optical amplifier chips; and
coupling light from the at least two semiconductor optical amplifier chips into the catheter.

25. A method as claimed in claim 24, wherein the step of inserting the catheter comprises inserting the catheter into a lumen of the patient.

26. A method as claimed in claim 24, wherein the step of inserting the catheter comprises inserting the catheter into a blood vessel of the patient.

27. A method as claimed in claim 24, wherein the step of inserting the catheter comprises inserting the catheter into a blood vessel to a heart of the patient.

28. A method as claimed in claim 24, further comprising packaging the at least two semiconductor optical amplifier chips into at least two pigtailed optoelectronic modules.

29. A method as claimed in claim 24, wherein the at least two semiconductor optical amplifier chips have different gain bandwidths.

30. A method as claimed in claim 24, wherein the step of coupling light from the at least two semiconductor optical amplifier chips into the catheter comprises coupling light between at least one frequency selective tunable element and the at least two semiconductor optical amplifier chips and the catheter.

31. A method as claimed in claim 24, further comprising polarization combining light from the at least two semiconductor optical amplifier chips and providing the light to the at least one frequency selective tunable element.

32. A method as claimed in claim 24, further comprising selectively coupling the at least two semiconductor optical amplifier chips to at least one frequency selective tunable element and an output coupler.

33. A method as claimed in claim 24, further comprising a multiplexing and demultiplexing light from the at least two semiconductor optical amplifier chips and providing the light to at least one frequency selective tunable element.

34. A method as claimed in claim 24, further comprising attenuating a level of the light provided to the catheter.

35. A method as claimed in claim 24, further comprising feeding back light into the at least two semiconductor optical amplifier chips serially in time.

36. A method as claimed in claim 24, further comprising feeding back light into the at least two semiconductor optical amplifier chips simultaneously.

37. A method as claimed in claim 24, wherein the step of controlling a frequency of light fed back into the at least two semiconductor optical amplifier chips comprises modulating an angle of a diffraction grating relative to light from the at least two semiconductor optical amplifier chips.

38. A widely tunable source, comprising:
- a first pigtailed semiconductor optical amplifier module with a first gain bandwidth;
- a second pigtailed semiconductor optical amplifier module with a second gain bandwidth;
- a frequency selective tunable element coupled to a first pigtail of the first pigtailed semiconductor optical amplifier module and a second pigtail of the second pigtailed semiconductor optical amplifier module, the frequency selective tunable element controlling a frequency of light fed back into the first pigtailed semiconductor optical amplifier module and the second pigtailed semiconductor optical amplifier module;
- an output coupler for coupling light from the first pigtailed semiconductor optical amplifier module and the second pigtailed semiconductor optical amplifier module into an output waveguiding device; and
- a controller for controlling the frequency selective tunable element in response to a wavelength of light in the output waveguiding device.

39. A widely tunable source as claimed in claim 38, wherein the frequency selective tunable element comprises a diffraction grating.

40. A widely tunable source as claimed in claim 39, further comprising a galvanometer for modulating an angle of the diffraction grating.

41. A widely tunable source as claimed in claim 39, further comprising a grating angle controller for modulating an angle of the diffraction grating relative to light from the first pigtailed semiconductor optical amplifier module and the second pigtailed semiconductor optical amplifier module.

42. A catheter system as claimed in claim 38, wherein the output coupler comprises an nxn coupler.

43. A widely tunable source as claimed in claim 38, wherein the output coupler comprises a splitter.

44. A widely tunable source as claimed in claim 38, further comprising a polarization combiner for combining light from the first pigtailed semiconductor optical amplifier module and the second pigtailed semiconductor optical amplifier module and providing the light to the at least one frequency selective tunable element.

45. A widely tunable source as claimed in claim 38, further comprising a switch for selectively coupling the first pigtailed semiconductor optical amplifier module and the second pigtailed semiconductor optical amplifier module to the frequency selective tunable element and the output coupler.

46. A widely tunable source as claimed in claim 38, wherein the first pigtailed semiconductor optical amplifier module and the second pigtailed semiconductor optical amplifier module comprise reflective semiconductor optical amplifier chips.

* * * * *